US00PP37158P2

(12) United States Plant Patent
Jackson et al.

(10) Patent No.: US PP37,158 P2
(45) Date of Patent: Dec. 16, 2025

(54) ***CERCIS* TREE NAMED 'JN106'**

(50) Latin Name: *Cercis canadensis*
Varietal Denomination: JN106

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 18/799,953

(22) Filed: Aug. 9, 2024

(51) Int. Cl.
*A01H 5/12* (2018.01)
*A01H 6/54* (2018.01)

(52) U.S. Cl.
USPC ..... Plt./216

(58) Field of Classification Search
USPC ..... Plt./216
CPC ... A01H 5/12; A01H 5/04; A01H 5/02; A01H 5/00; A01H 6/54
See application file for complete search history.

*Primary Examiner* — June Hwu
(74) *Attorney, Agent, or Firm* — Penny J. Aguirre

(57) ABSTRACT

A new cultivar of *Cercis canadensis* tree named 'JN106' that is characterized by its unique foliage colors; burgundy purple emerging foliage that change to dark green in color, its vigorous growth habit, and its well-branched plant habit.

2 Drawing Sheets

Botanical classification: *Cercis canadensis.*
Variety denomination: 'JN106'.

CROSS-REFERENCE TO RELATED APPLICATIONS

This application is co-pending with U.S. Plant Patent Applications filed for plants derived from the same breeding program that are entitled *Cercis* Tree Named 'JN100' (U.S. Plant patent application Ser. No. 18/799,941, *Cercis* Tree Named 'JN104' (U.S. Plant patent application Ser. No. 18/799,948), and *Cercis* Tree Named 'JN31' (U.S. Plant patent application Ser. No. 18/799,927.

BACKGROUND OF THE INVENTION

The present invention relates to a new and distinct cultivar of *Cercis canadensis* and will be referred to hereafter by its cultivar name, 'JN106'. 'JN106' is an Eastern redbud tree grown for use as a landscape plant.

The new *Cercis* was selected the new cultivar by the Inventors in summer of 2019 in a cultivated field in Belvidere, Tennessee. The field had been planted with seeds collected in 2016 and pooled from *Cercis canadensis* cultivars 'JN2' (U.S. Plant Pat. No. 21,451) and 'Ruby Falls' (U.S. Plant Pat. No. 22,097). As the two cultivars were the only cultivars growing in the area of seed collection, they are presumed to be the parent plants, however it is unknown which plants are the male or female parent.

Asexual propagation of the new cultivar was first accomplished by budding onto seedling understock of *Cercis canadensis* by one of the Inventors in August of 2019 in Belvidere, Tennessee. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JN106' as a unique cultivar of *Cercis*.

1. 'JN106' exhibits unique foliage colors; burgundy purple emerging foliage that change to dark green in color.
2. 'JN106' exhibits a vigorous growth habit.
3. 'JN106' exhibits a well-branched plant habit.

The probable parent plant, 'JN2', differs from 'JN106' in having yellow and tangerine emerging foliage and a faster growth habit with a greater susceptibility to wind and ice damage. The probable parent plant 'Ruby Falls' is similar to 'JN106' in having foliage that is burgundy purple in color. 'Ruby Falls' differs from 'JN106' in having a less vigorous growth habit with a less consistent branching habit.

'JN106' can also be compared to the co-pending cultivars of *Cercis canadensis* 'JN100', 'JN104' and 'JN31'. 'JN100' differs from 'JN106' in having foliage that emerges bright red and orange that changes to green in color and has a more upright plant habit. 'JN104' differs from 'JN106' in having foliage that is only green in color. 'JN31' differs from 'JN106' in having emerging foliage that is yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Website listings include but may not be limited to listings by Panther Creek Nursery and Sooner Plant Farm.

BRIEF DESCRIPTION OF THE DRAWINGS

The accompanying color photographs illustrate the overall appearance and distinct characteristics of the new *Cercis*.

The photographs were taken of a 3-year-old plant of the new cultivar as grown in a 5-gallon container in Belvidere, Tennessee.

Figure 1:
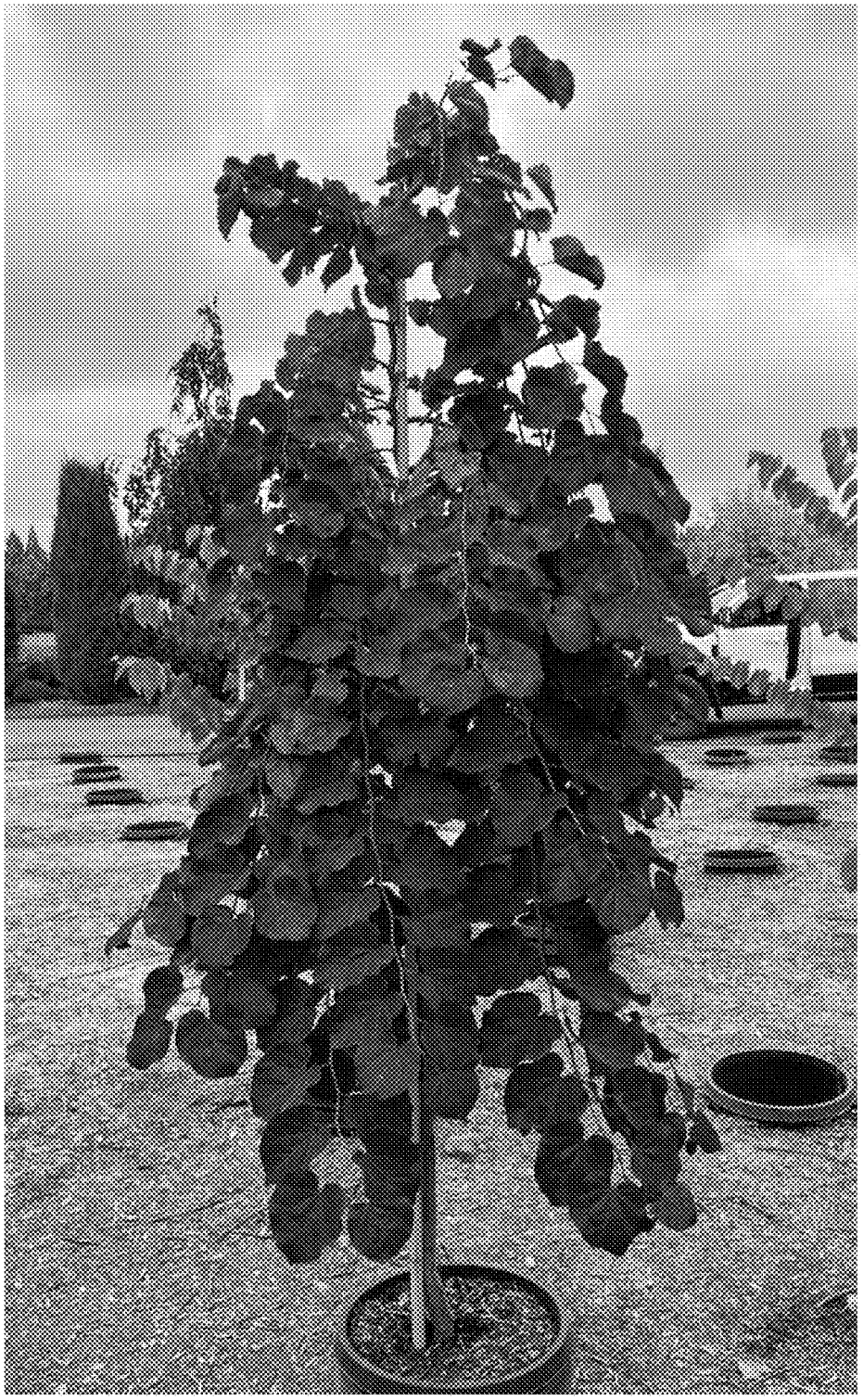

The photograph in FIG. 1 provides a view of the plant habit of 'JN106'.

Figure 2:
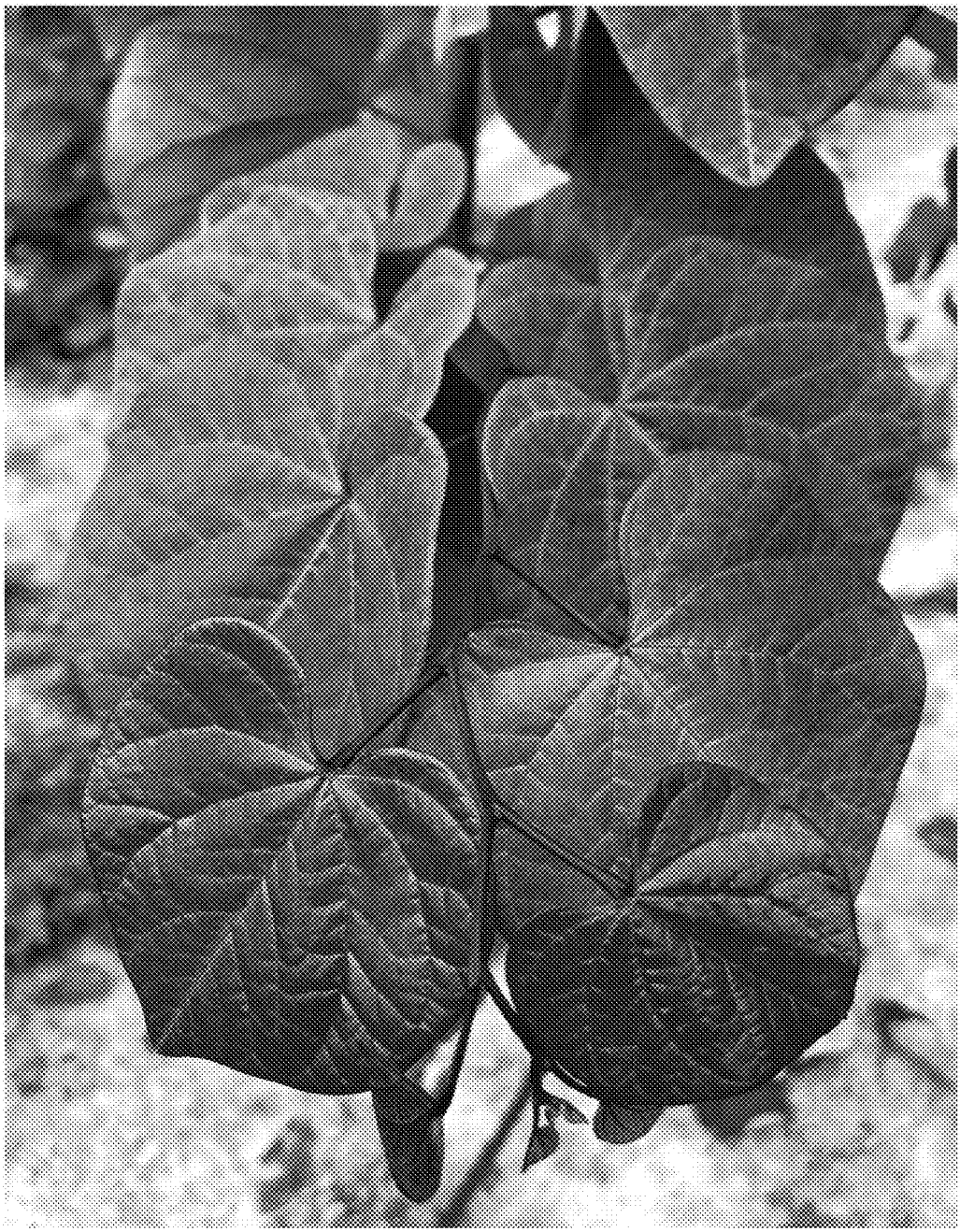

The photograph in FIG. 2 provides a close-up view of the foliage of 'JN106'.

The colors in the photographs are as close as possible with the digital photography techniques available, the color values cited in the detailed botanical description accurately describe the colors of the new *Cercis*.

DETAILED BOTANICAL DESCRIPTION

The following is a detailed description of a 3-year-old plants of the new cultivar as grown in a 5-gallon container in Belvidere, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—3 to 4 weeks in early spring in Belvidere, Tennessee.

*Plant type.*—Deciduous tree.

*Plant habit.*—Weeping and densely branched.

*Height and spread.*—Reaches between 1.8 m and 2.4 m in height and between 91 cm to 1.8 m in spread as a mature tree in the landscape.

*Cold hardiness.*—At least to U.S.D.A. Zone 5.

*Diseases and pests.*—No susceptibility or resistance to diseases or pests has been observed.

*Root description.*—Fibrous, 199A and N200B in color.

*Propagation.*—Budding.

*Propagation timing.*—Budding in July-August, growth begins in the spring and takes 7 months to become a salable whip.

*Growth rate.*—Vigorous.

Branch and trunk description:

*Trunk.*—An average of 35 cm in length (until lateral branching), 3 cm in diameter, surface; matte luster, relatively smooth, and very heavily lenticellate, color; N200A, very heavily covered with lenticels, 161A in color, lenticels cover most of trunk surface.

*Branch shape.*—Rounded, moderately zig-zag growth habit.

*Branch color.*—Emerging; 187A, young; a blend of 144A and 199A, mature; N200A, heavily covered with lenticels 155A in color, older bark; N200A, very heavily covered with lenticels, 161A in color.

*Branch size.*—Lateral branches; an average of 65 cm in length, 1 cm in diameter, tertiary branches (emerging branches); an average of 13 cm in length, 2 mm in diameter.

*Branch surface.*—Emerging and young; glabrous, glossy, mature; semi-glossy luster, relatively smooth, and heavily lenticellate; an average of 40 per sq·cm, oblong in shape, average of 2 mm in width and 3 mm in length, 161A in color, old bark; matte luster, relatively smooth, and very heavily lenticellate.

*Internode length.*—An average of 5 cm.

*Branching habit.*—1 main branch, 13 lateral branches per main branch, 16 tertiary branches per lateral branch.

Foliage description:

*Leaf shape.*—Reniform.

*Leaf division.*—Simple.

*Leaf base.*—Cordate.

*Leaf apex.*—Obcordate.

*Leaf fragrance.*—None.

*Leaf venation.*—Palmate, color; veins match surfaces of the leaf.

*Leaf margins.*—Entire, very slightly curled downward.

*Leaf arrangement.*—Alternate.

*Leaf aspect.*—Held reflexed downward from petiole (hanging) to outward.

*Leaf attachment.*—Petiolate.

*Leaf number.*—An average of 80 leaves per lateral stem.

*Leaf surface.*—Young; upper and lower surface; very glossy, glabrous, slightly transparent, mature; both surfaces matte, glabrous, and slightly transparent.

*Leaf size.*—An average of 9 cm in length and 8 cm in width.

*Leaf color.*—Emerging; upper and lower surface 152A, flushed with 187A, young; both surfaces a blend of 187A and 187B, mature; a blend of N186A and 187A on both surfaces and changing to 137B on upper surface and 138A with veins 187A on lower surface, fall; 162B on both surfaces.

*Petiole.*—An average of 10 cm in length and 1 mm in diameter, glabrous and glossy surfaces, flexible and moderately strong, color; emerging; 187A, young 197A, mature; a blend of 187A and N186A.

Inflorescence description:

*Inflorescence type.*—Cauliflorous clusters of papilionaceous (pea-like) flowers.

*Inflorescence size.*—Up to 5 cm in width and 3 cm in depth.

*Lastingness of inflorescence.*—2 to 3 weeks.

*Flower size.*—An average of 1.5 cm in length and 2 cm in width.

*Flower fragrance.*—Moderate.

*Flower number.*—An average of 13 flowers per cluster.

*Bracts.*—Average of 10, surrounding base of inflorescence, whorled, imbricate, ovate in shape, acute apex, an average of 0.75 mm in length and width, color; 145A, glabrous and slightly glossy surfaces.

*Peduncles.*—An average of 1.5 cm in length and 0.5 mm in diameter, color; 64C, slightly glossy surface, moderately strong, held straight from base, held at all directions from branch node in a whorled arrangement.

*Pedicels.*—None, peduncles attached in cluster at branch.

*Flower buds.*—Slightly curved, beak-shaped, 1 cm in length, 4 mm in width, glabrous and slightly glossy surfaces, color; 72B, veins N75B and 76B.

*Flower type.*—Papilionaceous.

*Calyx.*—Campanulate in shape, 4 mm in length, 3 mm in diameter.

*Sepals.*—5, 100% fused, 3 mm in length, entire margins, both surfaces are glabrous and slightly glossy, N80A in color.

*Corolla features.*—Papilionaceous, bilateral with two upper petals around the stamens and pistil, a center petal, and two lower petals under the center petal, upper petals; elliptic and cup shaped, margins slightly undulate, average of 9 mm in length, 6 mm in width, both surfaces glabrous, slightly glossy, color when opening and fully open; N75A, base 69D, center petal; 2 mm in length, 3 mm in width, both surfaces glabrous, slightly glossy, broad in shape and curled downward, rounded apex, cuneate base, entire margins, slightly undulate, color when opening and fully open; N75A, base 69D, veins 71A, lower petals; elliptical to in shape, curled downward, margins moderately undulate, average of 9 mm in length, 3 mm in width, both surfaces glabrous, slightly glossy and slightly transparent at the base, color when opening and fully open; N75A, base 69D.

Reproductive organs:

*Gynoecium*.—Pistil; 1, stigma; minute, indistinguishable, style; an average of 9 mm in length, 1 mm in width, N74B in color, ovary; round, in bottom of calyx, N80A in color.

*Androecium*.—Stamens; 10, anthers; club to oval shaped, an average of 0.4 mm in diameter, 200A in color, filament; an average of 4.5 mm in length and 0.5 mm in width, color; 69A, glossy and transparent surface, pollen is abundant in quantity, 11B in color.

*Seed and fruit*.—None observed to date.

It is claimed:

1. A new and distinct cultivar of *Cercis canadensis* tree named 'JN106' as herein illustrated and described.

* * * * *